(12) United States Patent
El-Bahr et al.

(10) Patent No.: US 11,767,360 B1
(45) Date of Patent: Sep. 26, 2023

(54) **ELISA FOR DIAGNOSIS OF *HAEMONCHUS LONGISTIPES* INFECTION IN CAMELS**

(71) Applicant: KING FAISAL UNIVERSITY, Al-Ahsa (SA)

(72) Inventors: Sabry Mohamed Bahy El-Bahr, Al-Ahsa (SA); El Awad M. El Hassan, Al-Ahsa (SA); Mohammad H. Al-Omran, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 17/941,212

(22) Filed: Sep. 9, 2022

(51) Int. Cl.
*C07K 16/18* (2006.01)
*G01N 33/569* (2006.01)

(52) U.S. Cl.
CPC ....... *C07K 16/18* (2013.01); *G01N 33/56966* (2013.01); *G01N 2333/4353* (2013.01); *G01N 2469/10* (2013.01)

(58) Field of Classification Search
CPC ..... G01N 33/56966; G01N 2333/4353; G01N 2469/10; C07K 16/18
See application file for complete search history.

(56) References Cited

PUBLICATIONS

Grodzki et al. Antibody Purification: Affinity Chromatography—Protein A and Protein G Sepharose: Chapter 5: pp. 33-41. Immunocytochemical Methods and Protocols Third Edition. Methods in Molecular Biology vol. 588. C. Oliver and M.C. Jamur eds. Humana Press (2010).*

El Hassan et al. Antigenic and Immunogenic Components of Haemonchus longistipes Identified by Western Immunoblotting. American Journal of Biochemistry and Biotechnology. 8 (3): 164-170 (2012).*
El-Bahy et al. Value of Haemonchus longistipes Purified Antigen in Diagnosis of Gastro-Intestinal Nematodes Infection. Pakistan Journal of Biological Sciences 10 (9): 1452-1458 (2007).*
Engvall, E. & Perlmann, P., "Enzyme-Linked Immunosorbent Assay, Elisa," J. Immun. 109(1): pp. 129-135 (1972).
Hassan, E. and El Bahr, S. M., "Antigenic and Immunogenic Components of Haemonchus longistipes Identified by Western Immunoblotting," Am. J. Biochem. & Biotech. 8(3): pp. 164-170 (2012).
Petit, A. et al., "Circulating Antigens in Ovine Hamonchosis," Ann. Rech. Vet. 12(1): pp. 1-9 (1981).
Cai, Y. et al., "FIeld comparison of circulating antibody assays versus circulating antigen assays for the detection of schistosomiasis japonica in endemic areas of China," Parasites & Vectors, 7: 138 (2014).
El-Bahy, M. M., et al., "Value of Haemonchus longistipes Purified Antigens in Diagnosis of Gastro-intestinal Nematodes Infection in Camels," Pakistan Journal of Biological Sciences 19(9): pp. 1452-1458 (2007).

\* cited by examiner

*Primary Examiner* — Gailene Gabel
(74) *Attorney, Agent, or Firm* — Nath, Goldberg & Meyer; Richard C. Litman

(57) ABSTRACT

An ELISA for the diagnosis of *Haemonchus longistipes* infection in camels is provided. The ELISA for the diagnosis of *Haemonchus longistipes* infection in camels includes antibodies raised against a 76 kDa protein isolated from *Haemonchus longistipes*. The resulting antibodies may be used in assays to detect *Haemonchus longistipes* infected camels. The assays may be any kind of enzyme-linked immunosorbent assay, or "ELISA", known to those of skill in the art. The assay using the antibodies raised against a 76 kDa protein isolated from *Haemonchus longistipes* infected camels may be capable of detecting pre-patent *Haemonchus longistipes* infection.

7 Claims, 2 Drawing Sheets

ELISA FOR DIAGNOSIS OF *HAEMONCHUS LONGISTIPES* INFECTION IN CAMELS

BACKGROUND

1. Field

The disclosure of the present patent application relates to an Enzyme-Linked Immunosorbent Assay (ELISA) for the diagnosis of *Haemonchus longistipes* infection in camels, and particularly to an antigen-ELISA utilizing antibodies to a 76 kDa protein isolated from *Haemonchus longistipes* and methods of using said ELISA to diagnose current and pre-patent infection with *Haemonchus longistipes*.

2. Description of the Related Art

Haemonchosis is a serious parasitic disease of camels and represents one of the major constrains to development of camel production. The disease is caused by *Haemonchus longistipes* and is widely distributed in tropical and subtropical regions including Saudi Arabia. The prevalence of this parasite has reached 13.6% in Al-Ahsa area of Eastern Saudi Arabia. The worm is a blood sucking abomasal nematode causing severe anemia, which may be fatal particularly to young animals. The worm starts to suck the blood of its host when it reaches the fourth stage larvae. Therefore, detection of early infection is essential to minimize the effect of this worm on camel health.

Diagnosis of pre-patent infection has not been attempted to date, although both fourth stage larvae and immature worms are bloodsuckers. Diagnosis is mainly made by parasitological techniques such as fecal floatation, fecal culture, and identification of infective larvae. This approach detects only patent infection and is time consuming. Molecular diagnosis using polymerase chain reaction "PCR" to detect the presence of parasites or eggs, although sensitive and specific, again detects only patent infection.

The immunodiagnostic ability of purified *Haemonchus longistipes* antigens to detect anti-parasite antibodies in naturally infected camels has previously been explored. (El-Bahy et al., "Value of *Haemonchus longistipes* purified antigens in diagnosis of gastro-intestinal nematodes infection in camels," J. of Biological Sci. 10(9): pp. 1452-1458 (2007)) Prior studies, however, have not revealed how to discriminate between current and previous infection.

Thus, an ELISA and methods of using said ELISA to diagnose current and pre-patent infection with *Haemonchus longistipes* are desired.

SUMMARY

An ELISA for diagnosis of *Haemonchus longistipes* infection in camels includes antibodies raised against a 76 kDa protein isolated from *Haemonchus longistipes* infected camels. The resulting antibodies may be used in assays to detect *Haemonchus longistipes* infected camels. The assays may be any kind of enzyme-linked immunosorbent assay, or "ELISA", known to those of skill in the art. As a non-limiting example, the ELISA may be an ELISA, a Sandwich ELISA, a Competitive ELISA, or a Reverse ELISA. The assay using the antibodies raised against a 76 kDa protein isolated from *Haemonchus longistipes* infected camels may be capable of detection of current and pre-patent infection with *Haemonchus longistipes*.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
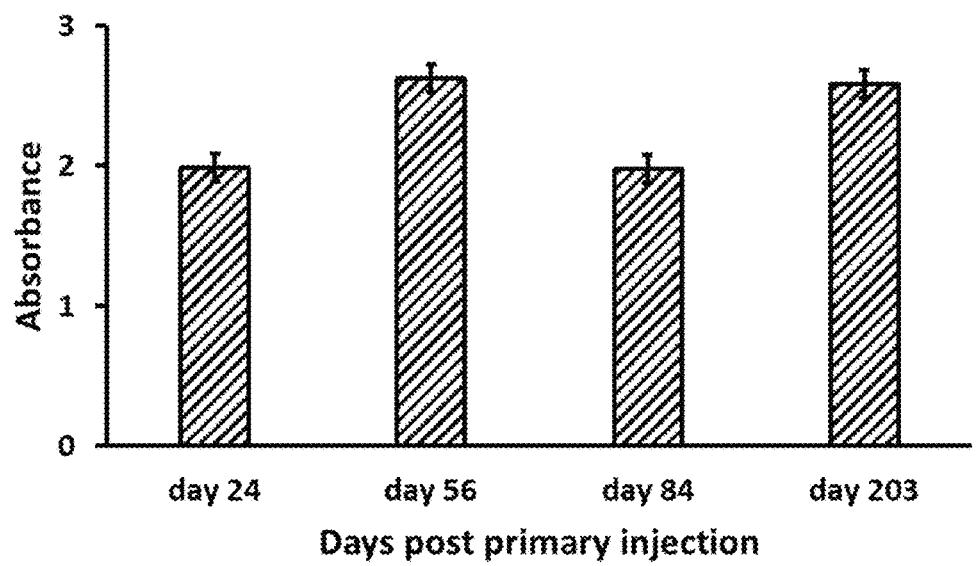
FIG. 1 is a graph depicting the antibody response in immunized rabbits.

An ELISA for the diagnosis of *Haemonchus longistipes* infection in camels includes antibodies raised against a 76 kDa protein isolated from *Haemonchus longistipes* infected camels. The resulting antibodies may be used in assays to detect *Haemonchus longistipes* infected camels. The assays may be any kind of enzyme-linked immunosorbent assay, or "ELISA", known to those of skill in the art. As a non-limiting example, the ELISA may be an ELISA, a Sandwich ELISA, a Competitive ELISA, or a Reverse ELISA. The assay using the antibodies raised against a 76 kDa protein isolated from *Haemonchus longistipes* infected camels may be capable of detection of current and pre-patent infection with *Haemonchus longistipes*.

As used herein, "pre-patent infection" refers to the period of a parasitic infection falling between the initial infection with the parasite and the point where infection with the parasite may be determined by recovering an infective form of the parasite, such as an oocyst or an egg from the blood or feces.

As used herein, "ELISA" refers to an enzyme-linked immunosorbent assay, a solid-phase enzyme immunoassay commonly used to detect the presence of a particular ligand. In the simplest form, antigens from a sample to be tested are attached to a surface, an antibody specific to an antigen of interest and linked to an enzyme are applied to the surface to allow binding to the antigen, unbound antibodies are removed, and a reagent containing the substrate of the antibody bound enzyme is added. If the antibody bound to the antigen of interest, the subsequent reaction produces a detectable signal (including but not limited to a color change), which is indicative of the presence of the antigen of interest in the sample.

In alternative embodiments the antibody may not be directly bound to the enzyme but may in turn be recognized by a second antibody which is bound to the enzyme. In further alternative embodiments, the ELISA may be a "Sandwich ELISA", a "Competitive ELISA", or a "Reverse ELISA".

In a Sandwich ELISA, a surface is first prepared with a known quantity of capture antibody. Non-specific binding sites on the surface are blocked and a sample containing antigens is applied to the plate allowing any target antigens to be captured by the antibody. The plate is washed to remove unbound antigen. A further specific antibody is then added that binds to the target antigen. Enzyme-linked secondary antibodies are then applied as detection antibodies, where the enzyme-linked secondary antibodies bind specifically to the further specific antibody's Fc region. The surface is washed to remove unbound antibody and a reagent is added to produce a detectable reaction with the enzyme.

In a Competitive ELISA, unlabeled primary antibody is incubated in the presence of a sample that may contain the antibody's target antigen. Any resulting bound primary antibody/antigen complexes are then added to an antigen-coated well. The plate is then washed to remove unbound antibodies. A second antibody coupled to an enzyme, specific to the primary antibody is added, and the plate is washed to remove unbound antibodies. The substrate is added and allowed to react with the enzyme bound to the second antibody. In this assay, the more antibody is bound up by antigen in the sample, the less antibody is available to bind to the plate. Thus, a stronger signal is associated with a lower quantity or absence of antigen in the sample.

In a Reverse ELISA, the antigens remain suspended in a testing fluid. Tagged antibody is incubated in the presence of a sample that may contain its target antigen. The sample is then passed through a "Scavenger" container. The surface of the Scavenger container has Scavenger antigens bound to it, which are specific to the antibody and bind any unbound/excess antibody. The resulting solution is then passed through a detector capable of detecting the tag.

In experiment, hyperimmune rabbit serum was synthesized according to methods previously described by Hassan & El Bahr, the entirety of which is incorporated herein by reference. (Hassan, E. and El Bahr, S. M., "Antigenic and Immunogenic Components of *Haemonchus longistipes* Identified by Western Immunoblotting," Am. J. Biochem. & Biotech. 8(3): pp. 164-170 (2012). Briefly, adult *H. longistipes* worms were obtained from naturally infected slaughtered camels. The worms were homogenized, treated with protease inhibitors, and centrifuged to obtain a soluble extract. The soluble extract was then injected into rabbits to generate hyperimmune serum. The hyperimmune serum was then used in Western Blotting to identify *H. longistipes* proteins present, and a 76-kDa protein was eluted and used to raise polyclonal antibodies in rabbits. These polyclonal antibodies to the 76-kDa protein were then purified, optionally labelled, and used in the assays disclosed herein to detect the presence of *H. longistipes*.

Diagnosis of active parasitic infection in the host necessitated development of an assay capable of sufficient sensitivity for detecting and tracing individual parasite antigens. Antigen-capture ELISA is capable of detecting antigens in host blood and has been used successfully to detect circulating helminth antigens. A key element in this immunoassay is the availability of high specific antibody to detect the target antigen, as the sensitivity of this assay is dependent on the specific activity and high avidity of the antibody. Two types of antibodies that can be utilized in this assay to detect the target antigen include polyclonal antibodies in hyper-immune serum raised to a single antigen and monoclonal antibodies. The hyper-immune serum usually contains a high proportion of high affinity antibodies with high ability to bind antigen. The high affinity and high sensitivity of polyclonal antibodies makes them better reagents in immunoassays compared to monoclonal antibodies, which often have a low affinity. However, the successful production of polyclonal antibodies requires the availability of a highly purified antigen so that the antibody produced will be able to detect the target antigen in complex mixtures. The use of SDS-PAGE for purification of antigens in a whole gel stained with a light stain such as Coomassie blue, sodium acetate or copper chloride to locate the target antigen permits the separation of a single protein band with a minimum risk of contamination by nearby protein bands. Proteins trapped in polyacrylamide gel can then be electro-eluted from the polyacrylamide and used for immunization. In this experiment, polyclonal antibodies to H. *longistipes* 76 kDa antigen were purified from the worm extract through a combination of SDS-PAGE and electro-elution.

Immunization of rabbits with the *H. longistipes* 76 kDa antigen eluted from Coomassie stained polyacrylamide gels elicited strong antibody response to this antigen when tested by antibody-ELISA. This result indicates that the 76 kDa antigen retained its immunogenicity and confirms the usefulness of the SDS-PAGE for the purification of protein antigens for immunization, as reported previously.

The 76 kDa antigen was found to be conserved between different species of nematodes, as antibodies raised to it reacted with both *H. longistipes* and Nematodirus sp. The cross reactivity among different helminthes is common and represents one of the limiting factors for the development of serological tests against helminth infection. However, serum raised to this antigen did not react with Cestodes' materials as it did not recognize Hydatid cyst fluid.

In developing immunoassay for the detection of antigens, purified antibodies are usually required as the efficiency of these assays is directly dependent on the purity of the antibody. Enrichment of antibodies may be achieved by any method known in the art (including but not limited to affinity chromatography with protein A sepharose). In this experiment, H. *longistipes* antibodies were separated from serum using affinity chromatography with protein A sepharose. The column eluate contained the desired antibody as judged by its ability to recognize the crude soluble extract of *H. longistipes* in ELISA.

Purified antibodies were then labelled. Although any suitable labeling method known in the art can be used, the purified IgG antibodies were labelled with horseradish peroxidase using the modified periodate method (Wilson and Nakane, 1978). This is a well-established method for conjugation of the enzyme, which preserves antibody reactivity by coupling to the carbohydrate portion of the enzyme and antibody molecule, which is not usually involved in the antigen binding (Liddell and Cryer, 1991). Conjugates produced by this method usually have higher activity than those produced by the two-step glutaraldehyde method with Nygren (1982) reporting five-fold higher detectability in spot-ELISA with periodate conjugates compared with those produced with the two-step glutaraldehyde method. The usefulness of protein A affinity chromatography for the separation of IgG from serum was confirmed. The IgG after conjugation to horseradish peroxidase retained its activity and could be used in antigen-trapping ELISA at high working dilution for subsequent studies monitoring the presence of the 76 kDa antigen in serum of infected animals.

The basic assay developed using anti-76 kDa conjugate effectively discriminated between crude soluble extract of *H. longistipes* and the control wells containing normal rabbit serum. The use of a blocking step (Towbin et al, 1979) in the basic assay to block the remaining sites of the solid matrix and incorporation of a blocking agent in the conjugate dilution buffer greatly reduced the background levels encountered in such assay. After establishing the appropriate working dilutions, the developed assay was then evaluated for detection of corresponding antigen in the serum of naturally infected camels. The assay was able to detect the target antigen in the serum of eight (40%) of the slaughtered camels. Seventy five percent of these antigen positive cases were not harboring adult worms in their gastro-intestinal tract as revealed by fecal examination, indicating pre-patent infection. Although fecal examination revealed strongyle eggs in 70% of the examined camels, this does not reflect *H. longistipes* infection since all strongyle group worms have similar eggs morphology (Urquhart et al, 1996). The anti-76 kDa antibodies produced in the present study recognized the soluble extract of Nematodirus sp. in antibody-ELISA, but not in the serum of infected camels. This could be attributed to the hypothesis that the Nematodirus sp. antigen that shares one or more similar epitopes with the 76 kDa molecule is a somatic protein in this parasite and not circulating in the blood of the infected animals. Such an antigen could have been released by physical disruption in the soluble extract of the parasite that was used in the antibody-ELISA. These data may also suggest that the *H. longistipes* 76 kDa antigen is a secretory/excretory product and is shared between the adult and juvenile stages as indicated by its presence in pre-patent infection.

In an embodiment, an *H. longistipes* specific antibody may be generated by a process including the steps of (1) preparing *H. longistipes* crude extract; (2) isolating an approximately 76 kDa protein from the *H. longistipes* crude extract; (3) raising antibodies against the approximately 76 kDa protein in a non-camelid mammal; and (4) purifying antibodies from the non-camelid mammal. In an embodiment, the *H. longistipes* crude extract may be generated from *H. longistipes* isolated from infected camels in Saudi Arabia.

In a further embodiment, the approximately 76 kDa protein may be purified before it is used to raise antibodies in the non-camelid mammal. The approximately 76 kDa protein may be purified by any method known in the art, and in a non-limiting example may be purified by separation on SDS-page gels, excision, electrophoretic elution, and concentration.

In a further embodiment, the non-camelid mammal may be a rabbit.

In a further embodiment, the step of raising antibodies against the approximately 76 kDa protein may include immunization and boosting steps. In a non-limiting example, this step may include immunizing a rabbit with 100 μg antigen emulsified in FCA on day 0 and day 14, and with further boosters of 50 μg on day 49 and 77, and a final boost of 25 μg of antigen on day 196. Serum containing the antibodies against the approximately 76 kDa protein may be collected on day 24, day 56, day 84, day 203, or day 210.

In a further embodiment, the purification of antibodies from the non-camelid mammal may include affinity chromatography. In a non-limiting embodiment, the affinity chromatography may be achieved using a Protein A Antibody Purification Kit.

In a further embodiment, the *H. longistipes* specific antibody generated by any of the methods discussed herein may be lyophilized. In a non-limiting example, the *H. longistipes* specific antibody may be dialyzed with slow stirring overnight against distilled water and then freeze-dried overnight to obtain lyophilized *H. longistipes* specific antibody.

In an embodiment, a *H. longistipes* specific antibody produced by any of the methods disclosed herein may be used to screen camels for infection with *H. longistipes*. In an embodiment this screening may include the steps of: (1) obtaining a sample from a camel in need of screening for *H. longistipes* infection; (2) exposing the sample to a *H. longistipes* specific antibody raised against a 76-kDa *H. longistipes* antigen; (3) measuring the degree of binding of the *H. longistipes* specific antibody to the sample; and (4) if a detectable level of binding occurs, administering a treatment for *H. longistipes* to the camel.

The present disclosure may be better understood in view of the following examples, which are illustrative only and are not intended to limit the present teachings.

EXAMPLE 1

Preparation of *H. longistipes* Crude Extract

Adult *Haemonchus longistipes* worms were obtained from the abomasa of naturally infected slaughtered camels at Al-Ahsa Central Abattoir and Alomran slaughterhouse, in the Kingdom of Saudi Arabia, following the method of Smith and Smith. (Smith & Smith, "Immunisation of sheep with an integral membrane glycoprotein complex of *Haemonchus contortus* and with its major polypeptide components," Res. Vet. Sci. 60: pp. 1-6 (1996)). The examined abomasa contained only *H. longistipes* parasites. Three hundred female and two hundred male worms were collected and identified by their barber pole appearance and long spicules.

*H. longistipes* worms were homogenized in 5 ml phosphate buffer saline "PBS" containing a mixture of protease inhibitors (Sigma Chemical Company, UK). The homogenate was centrifuged for one hour at 4° C. at 13000 rpm using a SORVALL RG3 Centrifuge (Thermo Scientific) and the supernatant was collected as a crude soluble extract. The protein concentration of this crude soluble extract was determined using QuantiProTM BCA assay kit (Sigma Chemical Company, UK) following manufacturer instructions and stored at −20° C. Prior to storage, the extract was diluted with an equal volume of Bio-Rad Laemmli sample buffer and heated to 100° C. for 5 minutes. This was then cooled to room temperature, centrifuged at 10000 rpm for 5 minutes, aliquoted into 200 μl volumes and stored at −20° C. until needed.

EXAMPLE 2

Purification of the 76 kDa Antigen and Antibodies

Ten Coomassie blue stained 7-20% gradient SDS-PAGE gels of *H. longistipes* soluble extracts produced according to Example 1 were used to provide materials for immunization. A 76 kDa protein was located and excised from each gel by reference to a molecular weight standard lane. The 76 kDa protein was then electrophoretically eluted from the excised gel portion using an electro-elution device (Model 422 Electro-Eluter, Bio Rad. USA) following the manufacturer's instructions. All electro-eluates were pooled and dialyzed overnight against phosphate-buffered saline (PBS) using a dialysis tube (M.W. cut-off 12000 Daltons, Sigma chemical Co. St. Louis, USA). The concentration of the dialyzed protein was determined using QuantiProTM BCA assay kit (Sigma Chemical Company, UK). This dialyzed protein was concentrated ~6-fold using a Centrifugal Ultrafiltration System (Sartorius Ltd., Germany) and stored at −20° C. until needed.

Antibodies to the purified 76 kDa antigen were produced in rabbits. All rabbits were maintained and handled in accordance with national guidelines and protocols approved by King Faisal University Scientific Research Ethics Committee. Each rabbit was injected intramuscularly with 100 μg antigen emulsified in Complete Freund's Adjuvant (FCA) on day 0 and on day 14. Two booster doses of 50 μg antigen in Incomplete Freund's Adjuvant (FIA) were administered to each rabbit subcutaneously on day 49 and 77 and a final boost of 25 µg of antigen in FIA on day 196. Serum was collected from these rabbits on days −1, 24, 56, 84, 203 and 210.

The amount of antibody in the sera collected from the rabbits on days 24, 56, 84 and 203, post primary injection of the antigen was measured by antibody-ELISA and the titer of the final serum collected on day 210 was also determined by the same assay. A dilution of 1/80 of *H. longistipes* crude soluble extract was used in the assay as antigen. Sera collected on days 24-203 were tested over a 2-fold dilution range from 1/250-1/8000, while the final serum was tested over a 2-fold dilution range from 1/500-1/1024000. Pre-immunization serum at a similar dilution range was included as a negative control in each case. Serum samples were tested in duplicate and those showing an absorbance value greater than two standard deviations (2xSDEV) above the mean of the negative control were considered positive. The antibody titer of the final serum was taken as the last dilution that continued to show an absorbance value greater than 2xSDEV above the mean of the negative control.

Figure 2:
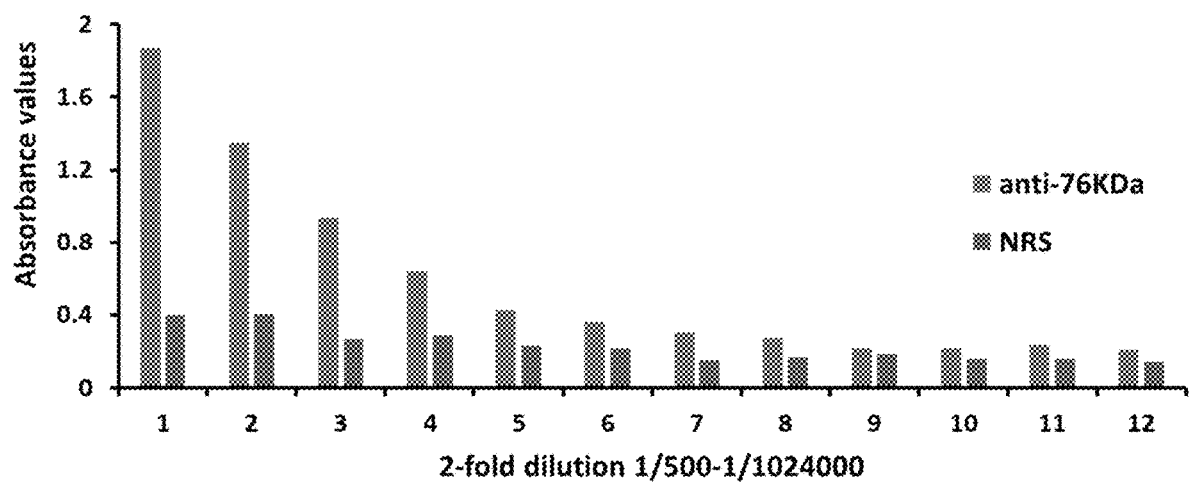
FIG. 2 is a graph depicting antibody titer in final serum collected on day 210 post-primary injection of antigen.

Serum from test bleeds collected from the immunized rabbits 10 days following each injection of the antigen showed a progressive increase in absorbance values when tested by ELISA against a soluble extract of the homologous population of *Haemonchus longistipes*. (See FIG. 1) At a serum dilution of 1/250 approximately 4-fold increase in the absorbance value from day 24 to day 203-post primary injection was observed. The anti-serum showed an absorbance value of 0.624 at day 24 which increased to 2.626 at day 203. (See FIG. 1) The antibody titer of the final serum raised to the 76 kDa antigen collected on day 210, post immunization, showed an absorbance value greater than 2xSDEV above the mean of negative control serum, was 1/1024000 as defined by antibody ELISA against the homologous H. *longistipes* soluble extract. (See FIG. 2)

EXAMPLE 3

Specificity of the α-76 kDa Antigen and Antibodies

The specificity of the day 210 serum collected from rabbits immunized with the 76 kDa antigen was examined by ELISA testing against soluble extracts of *H. longistipes* population, Nematodirus sp., and hydatid cyst fluid coated at a dilution of 1/80 in carbonate/bicarbonate buffer. The serum was tested at a dilution of 1/1000. Pre-immunization serum at a dilution of 1/1000 and PBS/Tween were also included in the plate as controls. The test samples showing an absorbance value greater than 2xSDEV above the mean of the negative control were considered positive.

Figure 3:
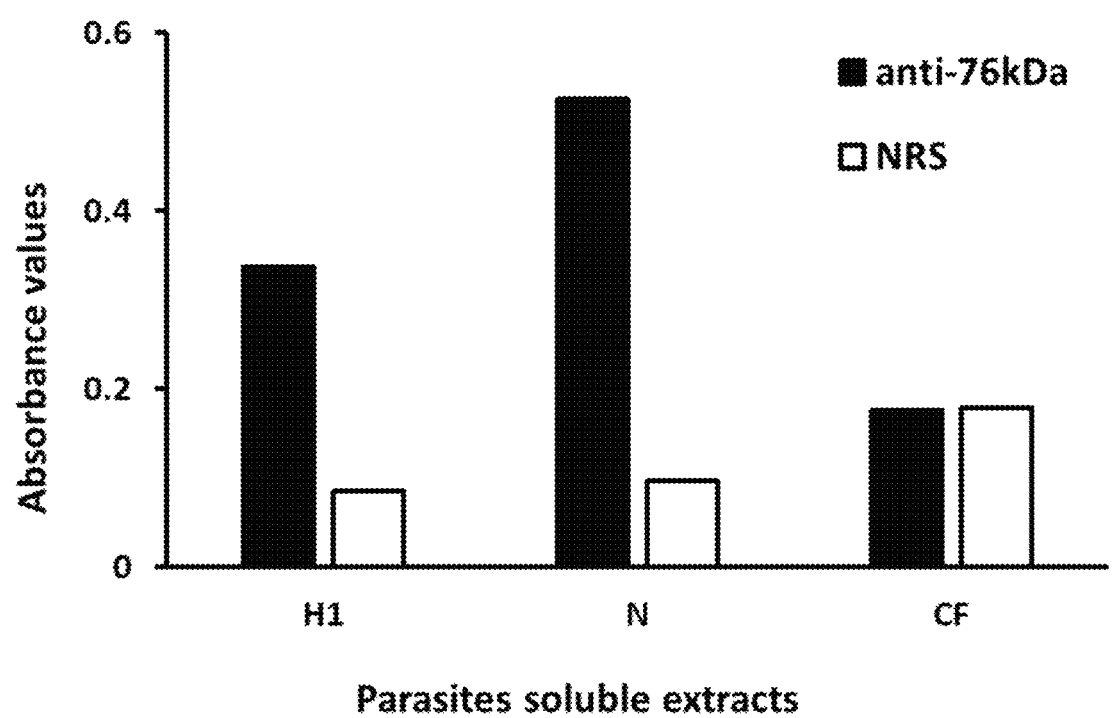
FIG. 3 is a graph depicting the specificity of the day 210 sera, wherein H1 reflects the *H. longistipes* homologous population, N reflects the results for Nematodirus spp., and CF reflects the results for Hydatid cyst fluid.

The serum reacted with the *H. longistipes* population, giving an absorbance value of more than 4× that of pre-immunization serum and with Nematodirus spp. giving an absorbance value of more than 6× that of pre-immunization serum. (See FIG. 3) In case of the hydatid cyst, fluid absorbance values of less than 2xSDEV above the mean of the pre-immunization serum were obtained.

EXAMPLE 4

Manufacturing and In Vitro Testing of the ELISA Assay

Anti-76 kDa protein antibodies synthesized according to Example 2 were purified by affinity chromatography using the commercially available Protein A Antibody Purification Kit (Sigma Chemical Company, UK) following the manufacturer instructions. The method utilized a 1.0 ml cartridge of immobilized protein A together with a Desalting Cartridge. The purified immunoglobulin was then dialyzed overnight against PBS at 4° C. with gentle shaking, its protein concentration measured using QuantiProTM BCA assay kit (Sigma Chemical Company, UK) and stored at −20° C. until needed. Part of the resulting IgG fraction was purified by affinity chromatography and dialyzed with slow stirring overnight against several changes of distilled water at 4° C. and another part of the resulting IgG fraction was purified and freeze-dried overnight using a freeze-dryer (LABCONCO, USA).

IgG antibody concentration in the elute of each run of protein A affinity column was 145 mg/ml when measured by QuantiProTM BCA Assay kit (Sigma Chemical Company, UK).

Both the dialyzed and the lyophilized IgG fractions were tested for reactivity against the 76 kDa antigen by antibody-ELISA. The antigen was used at 1/100 dilution. The IgG preparations were tested at eight 2-fold dilutions from 1/100 to 1/12800. Normal rabbit serum at a similar dilution series was also included in the test as a negative control. IgG dilution showing an absorbance value greater then 2xSDEV above the mean of the similar dilution of the negative control was considered positive.

The ELISA absorbance values of the dialyzed protein A column elute decreased with increasing dilutions of the antibody when titrated against soluble extract of the 76 kDa fraction of *H. longistipes*. An absorbance of 3.189 at a dilution of 1/100 was seen in this elute, which decreased to 0.121 at a dilution of 1/12800 (Table 1) but still more than 2xSDEV above the mean of the normal rabbit serum. On the other hand, lyophilized antibody prepared from this elute showed an absorbance value of 2.794 at a dilution of 1/100. This value decreased to 0.164 at antibody dilution of 1/12800, which was more than 2xSDEV above the mean of the normal rabbit serum, when titrated against the soluble extract of the 76 kDa fraction of H. *longistipes* using antibody-ELISA (Table 1).

TABLE 1

Anti-76kDa IgG purified by affinity chromatography: Reaction of dialyzed and lyophilized fractions with the 76kDa antigen by ELISA

| | Antibody dilution | | | | | | | |
|---|---|---|---|---|---|---|---|---|
| | 1/100 | 1/200 | 1/400 | 1/800 | 1/1600 | 1/3200 | 1/6400 | 1/12800 |
| Antigen dil. 1/100 | 1/100 | | | | | | | |
| Dialyzed IgG | 3.189 | 3.013 | 0.891 | 0.420 | 0.217 | 0.172 | 0.143 | 0.121 |
| Lyophilized IgG | 2.794 | 1.939 | 1.017 | 0.575 | 0.280 | 0.187 | 0.164 | 0.123 |
| NRS | 1.426 | 0.801 | 0.457 | 0.280 | 0.163 | 0.123 | 0.118 | 0.090 |
| 2SDEV + Mean | 1.501 | 0.802 | 0.469 | 0.290 | 0.186 | 0.124 | 0.138 | 0.092 |

The modified periodate method (Wilson and Nakane, 1978) was used to conjugate horseradish peroxidase (HRP) to the lyophilized anti-76 kDa IgG. The resulting IgG-HRP conjugate was dialyzed overnight against PBS at 4° C. Prior to storage, an equal volume of glycerol was added to the conjugate which was then stored at −20° C. until needed. The conjugated anti-76 kDa IgG then tested against crude soluble extract of the *H. longistipes* population and the purified 76 kDa antigen using direct ELISA. The coating antigens were used at a 2-fold dilution range from 1/50 to 1/400, while the conjugate was titrated at a 2-fold dilution range from 1/200 to 1/12800. PBS/Tween containing 0.5% non-fat dried milk (NFDM) was used as a negative control. The last conjugate dilution showing an absorbance value with both antigen preparations greater than 2xSDEV above the mean of the negative control was, considered as the working dilution of the conjugate.

A basic test procedure consisted of coating an ELISA microtiter plate with anti-76 kDa IgG. The plate was coated with a 100 μl/well of a 2-fold dilution of IgG from 1/50 to 1/6400, incubated overnight at 4° C., and washed. The remaining sites of the plate were blocked by adding 100 μl/well PBS/Tween containing 0.5% non-fat dry milk (NFDM) to each well, incubated for 30 minutes at 37° C. and washed. Each coating dilution was then reacted with 100 μl/well either *H. longistipes* soluble extract or normal rabbit serum (NRS) using a 2-fold dilution series from 1/50 to 1/400. The remaining area of the plate was incubated with 100 μl/well PBS/Tween containing 0.5% NFDM. After incubation for 30 minutes at 37° C. and washing, 100 μl/well of anti-76 kDa IgG labeled with HRP at a dilution of 1/200 in PBS/Tween containing 0.5% NFDM was added to each well. The plate then incubated for 30 minutes at 37° C. and washed before adding 100 μl/well of the 3,3',5,5'-tetramethylbenzidine (TMB) substrate. After incubation for 15 minutes at 37° C., the reaction was stopped by the addition of 50 μl/well of 2M sulfuric acid. The optical density of each well was read at 450 nm using an ELISA plate reading photometer (A.D.TOUCH, apDian.v. Belgium). The last coating IgG dilution reacted with the parasite extract and showing an absorbance value greater than 2xSDEV above the mean of the NRS was used as the working dilution of the coating IgG in subsequent assays.

Both *H. longistipes* crude soluble extract and the purified 76 kDa antigen when titrated against labelled anti-76 kDa IgG by direct ELISA reacted at 1/50 dilution with the labelled IgG diluted to 1/200 showing an absorbance value greater than 2xSDEV above the mean of PBS/Tween (Table 2). The purified 76 kDa antigen at a dilution of 1/100 reacted also with the labelled IgG diluted at 1/400 and again at a dilution of 1/400 reacted with the labelled IgG diluted to 1/1600. The crude soluble extract diluted to 1/200 and 1/400 reacted with the labelled IgG at 1/200 dilution (Table 2). As shown in Table 2 the labelled IgG dilution that reacted with both antigens was 1/200.

TABLE 2

Reactivity of labelled anti-76kDa IgG by direct ELISA

| | dil. | | Labelled | IgG dil. | | | | PBS/T |
|---|---|---|---|---|---|---|---|---|
| Antigen | 1/200 | 1/400 | 1/800 | 1/1600 | 1/3200 | 1/6400 | 1/12800 | 2xSDEV + M |
| 76kDa 1/50 | 0.102 | 0.059 | 0.056 | 0.051 | 0.055 | 0.063 | 0.072 | 0.090 |
| 76kDa 1/100 | 0.065 | 0.093 | 0.062 | 0.052 | 0.051 | 0.072 | 0.066 | 0.090 |
| 76kDa 1/200 | 0.071 | 0.063 | 0.057 | 0.056 | 0.068 | 0.082 | 0.056 | 0.090 |
| 76kDa 1/400 | 0.090 | 0.061 | 0.066 | 0.100 | 0.058 | 00.068 | 0.053 | 0.090 |
| Crude 1/50 | 0.134 | 0.071 | 0.079 | 0.063 | 0.071 | 0.062 | 0.058 | 0.085 |
| Crude 1/100 | 0.078 | 0.064 | 0.064 | 0.064 | 0.061 | 0.064 | 00.062 | 0.085 |
| Crude 1/200 | 1.028 | 0.075 | 0.066 | 0.069 | 0.060 | 0.064 | 0.066 | 0.085 |
| Crude 1/400 | 0.111 | 0.085 | 0.064 | 0.060 | 0.055 | 0.069 | 0.065 | 0.085 |

EXAMPLE 5

In Vivo Testing of the ELISA Assay

The assay was evaluated for its ability to detect *H. longistipes* antigens in naturally infected camels. The basic assay was performed by coating an ELISA microtiter plate overnight at 4° C. with unlabeled anti-76 kDa IgG at a dilution of 1/50 and then washing the plate. The remaining sites of the plate were blocked by adding 100 μl/well PBS/Tween containing 0.5% NFDM to each well, incubated for 30 minutes at 37° C. and washed. The bound IgG was then reacted with 100 μl/well of undiluted serum collected from 20 slaughtered camels coprologically examined for the presence of strongyle type eggs in their feces. The serum samples were tested in duplicates and a camel-calf serum was incorporated in the run as a negative control. Following incubation and washing, HRP-labeled anti-76 kDa IgG at a dilution of 1/200 was then added to each well and the assay was performed as described above. Serum samples showing an absorbance value greater than 2xSDEV above the mean of the negative control serum were considered positive for *H. longistipes* antigens.

At 1/50 dilution of all reagents the assay was able to discriminate between antigen and NRS (Table 3). This dilution was chosen as a working dilution of the unlabeled IgG. The peroxidase labelled anti-76 kDa IgG detected the *H. longistipes* antigen at a dilution of 1/400. In addition, a dilution of up to 1/6400 for the unlabeled IgG was able to react with the H. *longistipes* antigen at a dilution of 1/50 (Table 3).

TABLE 3

Determination of working dilution of unlabeled IgG

| | 1/50 | 1/100 | Coating 1/200 | IgG 1/400 | Dilutions 1/800 | 1/1600 | 1/3200 | 1/6400 |
|---|---|---|---|---|---|---|---|---|
| Ag 1/50 | 0.954 | 0.197 | 0.093 | 0.327 | 0.170 | 0.102 | 0.099 | 0.311 |
| Ag 1/100 | 0.204 | 0.335 | 0.164 | 0.090 | 0.195 | 0.207 | 0.109 | 0.114 |
| Ag 1/200 | 0.166 | 0.207 | 0.158 | 0.103 | 0.161 | 0.111 | 0.114 | 0.108 |
| Ag 1/400 | 0.171 | 0.937 | 0.126 | 0.104 | 0.084 | 0.264 | 0.085 | 0.117 |
| NRS 1/50 | 0.115 | 0.216 | 0.114 | 0.111 | 0.121 | 0.105 | 0.092 | 0.092 |
| NRS 1/100 | 0.186 | 0.218 | 0.139 | 0.119 | 0.131 | 0.100 | 0.081 | 0.089 |
| NRS 1/200 | 0.115 | 0.153 | 0.125 | 0.110 | 0.097 | 0.165 | 0.165 | 0.098 |
| NRS 1/400 | 0.099 | 0.142 | 0.106 | 0.103 | 0.111 | 0.122 | 0.083 | 0.157 |
| PBS/Tween 2xSDEV + M | 0.195 | 0.219 | 0.149 | 0.153 | 0.137 | 0.215 | 0.178 | 0.162 |

The developed assay was able to detect circulating *H. longistipes* antigens in the serum of eight (40%) of the 20 slaughtered camels. Six of these animals were not harboring strongyle eggs in their feces, while the other two were copro-positive as revealed by fecal flotation technique (Table 4).

TABLE 4

Antigenemia and parasitemia of the examined camels

| Animal identification | Antigenemia | Parasitemia |
|---|---|---|
| 1 | −ve | +ve |
| 2 | −ve | +ve |
| 3 | +ve | −ve |
| 4 | +ve | −ve |
| 5 | +ve | −ve |
| 6 | −ve | +ve |
| 7 | −ve | +ve |
| 8 | +ve | −ve |
| 9 | +ve | −ve |
| 10 | −ve | +ve |
| 11 | −ve | +ve |
| 12 | −ve | +ve |
| 13 | +ve | −ve |
| 14 | −ve | +ve |
| 15 | −ve | +ve |
| 16 | +ve | +ve |
| 17 | −ve | +ve |
| 18 | +ve | +ve |
| 19 | −ve | +ve |
| 20 | −ve | +ve |

It is to be understood that the ELISA for the diagnosis of *Haemonchus longistipes* infection in camels is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of producing a *Haemonchus longistipes* (*H. longistipes*) specific antibody, comprising the steps of:
   (1) preparing *H. longistipes* crude extract;
   (2) isolating an approximately 76 kDa protein from the *H. longistipes* crude extract;
   (3) purifying the approximately 76 kDa protein by Sodium dodecyl-sulfate polyacrylamide gel electrophoresis (SDS-page) and electro-elution;
   (4) raising antibodies against the approximately 76 kDa protein in a non-camelid mammal; and
   (5) purifying antibodies from the non-camelid mammal, wherein
   the step of raising antibodies against the approximately 76 kDa protein further comprises immunization and boosting steps, and
   the immunization step comprises injecting the non-camelid mammal with 100 µg of the 76 kDa protein on day 0 and day 14; and wherein the boosting step comprises injecting the non-camelid mammal with 50 µg of the 76 kDa protein on day 49 and 77, and a final injection of 25 µg of the 76 kDa protein on day 196.

2. The method of claim 1, wherein purifying the approximately 76 kDa protein comprises:
   separation of the approximately 76 kDa protein on a SDS-page gel;
   excision of the approximately 76 kDa protein;
   electrophoretic elution of the approximately 76 kDa protein; and
   concentration of the approximately 76 kDa protein.

3. The method of claim 1 wherein the non-camelid mammal is a rabbit.

4. The method claim 1, further comprising collecting serum from the non-camelid mammal on day 24, day 56, day 84, day 203, or day 210 after the immunization step.

5. The method of claim 1, wherein the antibodies are purified using affinity chromatography with protein A sepharose.

6. The method of claim 1, further comprising lyophilizing the *H. longistipes* specific antibody.

7. A *Haemonchus longistipes* (*H. longistipes*) specific antibody produced by the method of claim 1.